United States Patent [19]

Berg

[11] Patent Number: 5,385,649

[45] Date of Patent: Jan. 31, 1995

[54] SEPARATION OF 1-HEXENE FROM HEXANE BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 245,473

[22] Filed: May 18, 1994

[51] Int. Cl.⁶ .......................... B01D 3/36; C07C 7/06
[52] U.S. Cl. ...................................... 203/62; 203/63; 585/864
[58] Field of Search ..................... 203/63, 62; 585/864

[56] References Cited

U.S. PATENT DOCUMENTS

| | | | |
|---|---|---|---|
| 2,186,524 | 1/1940 | Frey et al. | 203/60 |
| 2,461,993 | 2/1949 | McKinnis | 203/62 |
| 3,087,866 | 4/1963 | Burch | 203/60 |
| 5,100,515 | 3/1992 | Lee et al. | 203/62 |

*Primary Examiner*—Wilbur Bascomb, Jr.

[57] ABSTRACT

1-Hexene is difficult to separate from hexane by conventional distillation or rectification because of the proximity of their boiling points. 1-Hexene can be readily separated from hexane by azeotropic distillation. Effective agents are 2-ethyl-1-butanol and diacetone alcohol.

1 Claim, No Drawings

SEPARATION OF 1-HEXENE FROM HEXANE BY AZEOTROPIC DISTILLATION

FIELD OF THE INVENTION

This invention relates to a method for separating 1-hexene from hexane using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

There are a number of commercial processes which produce mixtures hydrocarbons that boil very close together, e.g. petroleum refining and Fischer-Tropsch. Two close boiling compounds frequently produced are 1-hexene, b.p.=64° C. and hexane, b.p.=69°C. The relative volatility between these two is 1.07 which makes it virtually impossible to separate them by conventional rectification. Azeotropic distillation would be an attractive method of effecting the separation of 1-hexene from hexane if agents can be found that (1) will create a large apparent relative volatility between 1-hexene and hexane and (2) are easy to recover from 1-hexene. Table 1 shows the relative volatility required to obtain 99% purity. With no agent, the relative volatility is 1.07 and 181 actual plates are required. With an agent giving a relative volatility of 1.33, only 44 actual plates are required.

OBJECTIVE OF THE INVENTION

The object of this invention is to provide a process or method of extractive distillation that will enhance the relative volatility 1-hexene from hexane in their separation in a rectification column. It is a further object of this-invention to identify organic compound which in addition to the above constraints, are stable, can be separated from 1-hexene and recycled to the extractive distillation column with little decomposition.

TABLE 1

Theoretical and Actual Plates Required vs. Relative Volatility for 1-Hexene - Hexane Separation

| Relative Volatility | Theoretical Plates Required At Total Reflux, 99% Purity | Actual Plates Required 75% Efficiency |
|---|---|---|
| 1.07 | 136 | 181 |
| 1.20 | 50 | 67 |
| 1.30 | 35 | 47 |
| 1.33 | 33 | 44 |

SUMMARY OF THE INVENTION

The objects of this invention are provided by a process for the separation of 1-hexene from hexane which entails the use of certain organic compounds when employed as the agent in azeotropic distillation.

TABLE 2

Effective Azeotropic Distillation Agents For Separating 1-Hexene From Hexane

| Compounds | Relative Volatility |
|---|---|
| None | 1.07 |
| t-Butanol | 1.20 |
| Cyclopentanol | 1.20 |
| Diacetone alcohol | 1.33 |
| 2-Ethyl-1-butanol | 1.20 |

DETAILED DESCRIPTION OF THE INVENTION

I have discovered that certain organic compounds will greatly improve the relative volatility of 1-hexene from hexane and permit the separation of 1-hexene from hexane by rectification when employed as the agent in azeotropic distillation. Table 2 lists the compounds that I have found to be effective. They are t-butanol, cyclopentanol, diacetone alcohol and 2-ethyl-1-butanol.

THE USEFULNESS OF THE INVENTION

The usefulness or utility of this invention can be demonstrated by referring to the data presented in Tables 1 and 2. All of the successful agents show that 1-hexene can be separated from hexane by means of azeotropic distillation in a rectification column and that the ease of separation as measured by relative volatility is considerable.

WORKING EXAMPLES

EXAMPLE 1

Eighty grams of hexane, 20 grams of 1-hexene and 50 grams of 2-ethyl-1-butanol were charged to a vapor-liquid equilibrium still and refluxed for 13 hours. Analysis indicated a vapor composition of 29% 1-hexene, 71% hexane; a liquid composition of 25% 1-hexene, 75% hexane. This is a relative volatility of 1.22.

EXAMPLE 2

A solution comprising 60 grams of 1-hexene, 50 grams of hexane and 150 grams of diacetone alcohol was placed in the stillpot of a 5.5 theoretical plate glass perforated plate rectification column and operated at total reflux for five hours. The overhead composition was 69.6% 1-hexene, 30.4% hexane and the bottoms composition was 31.9% 1-hexene, 68.1% hexane. This gives a relative volatility of 1.33 for each theoretical plate.

I claim:

1. A method for recovering 1-hexene from a mixture of 1-hexene and hexane which comprises distilling a mixture of 1-hexene and hexane in the presence of an azeotrope forming agent, recovering the hexene-1 and the azeotrope forming agent as overhead product and obtaining the hexane as bottoms product; wherein said azeotrope forming agent consists of one material selected from the group consisting of t-butanol, cyclopentanol, diacetone alcohol and 2-ethyl-1-butanol.

* * * * *